US010139317B2

(12) United States Patent
Logue

(10) Patent No.: US 10,139,317 B2
(45) Date of Patent: Nov. 27, 2018

(54) METHODS AND APPARATUSES FOR TRACE AND ULTRATRACE ANALYSIS

(71) Applicant: South Dakota Board of Regents, Pierre, SD (US)

(72) Inventor: Brian Logue, Brookings, SD (US)

(73) Assignee: South Dakota Board of Regents, Pierre, SD (US)

( * ) Notice: Subject to any disclaimer, the term of this patent is extended or adjusted under 35 U.S.C. 154(b) by 260 days.

(21) Appl. No.: 14/928,694

(22) Filed: Oct. 30, 2015

(65) Prior Publication Data

US 2017/0122845 A1    May 4, 2017

(51) Int. Cl.
| | |
|---|---|
| *G01N 1/10* | (2006.01) |
| *B01D 9/04* | (2006.01) |
| *G01N 1/40* | (2006.01) |
| *G01N 1/42* | (2006.01) |
| *G01N 33/18* | (2006.01) |
| *B01D 15/02* | (2006.01) |
| *B01D 15/08* | (2006.01) |
| *B01D 9/00* | (2006.01) |
| *G01N 1/28* | (2006.01) |

(Continued)

(52) U.S. Cl.
CPC ............. *G01N 1/10* (2013.01); *B01D 9/0004* (2013.01); *B01D 9/04* (2013.01); *B01D 15/02* (2013.01); *B01D 15/08* (2013.01); *G01N 1/405* (2013.01); *G01N 1/42* (2013.01); *G01N 33/18* (2013.01); *G01N 33/1826* (2013.01); *B01F 13/0818* (2013.01); *G01N 2001/1068* (2013.01); *G01N 2001/2866* (2013.01); *G01N 2001/386* (2013.01); *G01N 2001/4033* (2013.01)

(58) Field of Classification Search
CPC .. G01N 1/10; G01N 33/18; G01N 2001/1068; B01D 15/02; B01D 15/08
See application file for complete search history.

(56) References Cited

U.S. PATENT DOCUMENTS

| | | |
|---|---|---|
| 4,265,920 A | 5/1981 | Thijssen |
| 2002/0098594 A1 | 7/2002 | Sandra et al. |
| 2016/0205959 A1* | 7/2016 | Kashiwagi ............... A23C 1/06 |

FOREIGN PATENT DOCUMENTS

| | | |
|---|---|---|
| EP | 0196128 A1 | 3/1986 |
| JP | H078812 A | 1/1995 |

(Continued)

OTHER PUBLICATIONS

Riu, J., et al, "Determination of Parts Per Trillion Level of Carboxylic Degradation Products of Linear Alkylbenzenesulfonates . . . ", vol. 50, No. 5/6, (Sep. 1999), p. 275-281. Sep. 30, 1999.

(Continued)

*Primary Examiner* — Hezron E Williams
*Assistant Examiner* — Xin Zhong
(74) *Attorney, Agent, or Firm* — McKee, Voorhees & Sease, PLC

(57) ABSTRACT

Methods of analyzing analytes from a liquid medium are disclosed. A system and apparatus for the analysis of analytes from a liquid medium are further disclosed. In particular, methods and apparatus of analyzing analytes by freezing liquid medium and partitioning the analyte into a sorptive stirrer are disclosed. Further, the methods and apparatus of the present invention can be useful in concentrating and isolating target chemicals of high value.

17 Claims, 16 Drawing Sheets

(51) Int. Cl.
G01N 1/38 (2006.01)
B01F 13/08 (2006.01)

(56) References Cited

FOREIGN PATENT DOCUMENTS

| | | |
|---|---|---|
| JP | 11216301 A | 8/1999 |
| JP | 2000124030 A | 4/2000 |
| JP | 2001009254 A | 1/2001 |
| JP | 2001286745 A | 10/2001 |
| WO | 0157515 A2 | 8/2001 |

OTHER PUBLICATIONS

Tomkins, Bruce A., et al, "Determination of N-Nitrosodimethylamine at Part-per-Trillion Levels in Drinking Waters and Contaminated Groundwaters", Analytical Chemistry, vol. 67, No. 23, (1995), p. 4387-4395. Dec. 1, 1995.
Yamishita, Nobuyoshi, et al, "Analysis of Perfluorinated Acids at Parts-Per-Quadrillion Levels in Seawater Using Liquid Chromatography-Tandem Mass Spectrometry", Environmental Science and Technology, vol. 38, No. 21, (2004), p. 5522-5528. Sep. 28, 2004.
Alzaga, Roberto, et al, "Accurate Determination of 2, 4, 6-Trichloroanisole in Wines at Low Parts Per Trillion by Solid-Phase Microextraction Followed by GC-ECD", Journal of Agricultural and Food Chemistry, vol. 51, p. 3509-3514. May 7, 2003.
Cardininali, Frederick L., et al, The Use of Solid-Phase Microextraction . . . , Journal of Chromatographic Science, vol. 38 (2000), p. 49-54. Feb. 28, 2000.
Klein, Dustin R., et al, Quantitative determination of triclocarban in wastewater effluent . . . , Journal of Chromatography A, vol. 1217, (2010), p. 1742-1747. Jan. 1, 2010.
Chary, N. Sridhara, et al, Parts per trillion level determination of endocrine-disrupting chlorinated compunds in river water . . . , vol. 404, (2012), p. 1993-2006. Aug. 1, 2012.
Subden, R.E., et al, "Determination of histamines in wines and musts by reversed-phase high-performance liquid chromatography", Journal of Chromatography, vol. 166, (1978), p. 310-312. Jan. 1, 1978.
"Solid Phase Microextraction with Thermal Desorption Using Fused Silica Optical Fibers", Analytical Chemistry, vol. 62, p. 2145-2146. Oct. 10, 1980.
Baltussen, Erik, et al, "Stir Bar Sorptive Extraction (SBSE), a Novel Extraction Technique for Aqueous Samples: Theory and Principles", vol. 11, No. 10, (1999), p. 737-747.ououoi Sep. 11, 1999.
Prieto, A., et al, "Sitr-bar sorptive extraction: A view on method optimisation, novel applications, limitations and potential solutions", Journal of Chromatography A, vol. 1217, (2010), p. 2642-2666. Jan. 4, 2010.
Miyawaki, Osato, et al, "Effective Partition Constant of Solute between Ice and Liquid Phases in Progressive Freeze-Concentration", Journal of Food Science, vol. 63, No. 4, (1998), p. 1-3. Jan. 1, 1998.
Fujioka, Ryosuke, et al, "Application of progressive freeze-concentation for desalination", Desalination, vol. 319, (2013), p. 33-37. Jan. 1, 2013.
Kobayashi, Atsuko, et al, "A Method for Making Large Agglomerated Ice Crystals for Freeze Concentation", Journal of Food Engineering, vol. 27, (1996), pp. 1-15. Jan. 1, 1996.
Heiss, Rudolph, et al, "Fundamentals of Freeze-Concentration of Liquids", Food Technology, (1949), p. 211-218. Aug. 1, 1949.
Liu, Ling, et al, "Progressive Freeze-Concentration of Model Liquid Food", Food Science Technology, vol. 3, No. 4, (1997), p. 348-352. Jun. 13, 1997.
Liu, Ling, et al, "Progressive Freeze-Concentration of Tomato Juice", Food Science Technology, vol. 5, No. 1, (1998), p. 108-112. Sep. 9, 1998.
Bayindirli, Levent, et al, "Mathematical Analysis of Freeze Concentration of Apple Juice", Journal of Food Engineering, vol. 19, (1993), p. 95-107. Jan. 1, 1993.
CRC Critical Reference in Food Science and Nutrition, vol. 20, Issue 3, pp. 214-248. Jan. 1, 1981.
Deshpande, S.S., et al, "Freeze Concentration of Fruit Juices", CRC Critical Reference in Food Science and Nutrition, vol. 20, Issue 3, pp. 173-213. Jan. 1, 1981.
Essery, R.E., et al, "The Concentration of Beer by Freezing", Institute of Brewing Research Laboratory, (1947), pp. 204-208. Aug. 1, 1947.
Halde, Rolf, "Concentration of Impurities by Progressive Freezing", Department of Chemical Engineering Design, vol. 14, pp. 575-580. Feb. 28, 1979.
Dai, Yingjie, et al, "Separation of Pollutants from Water Using The Freeze-Concentration Process", Environmental Engineering and Management Journal, vol. 10, No. 7, (2011), pp. 955-958. Jul. 1, 2011.
Miyawaki, Osato, et al, "Tubular ice system for scale-up of progressive freeze-concentration", Journal of Food Engineering, vol. 69, (2005), pp. 107-113. Jul. 13, 2004.
Novakova, Lucie, et al, "A review of current trends and advances in modem bio-analytical methods: Chromatography and sample preparation", Analytica Chimica Acta, vol. 656, (2009), pp. 8-35. Jan. 1, 2009.
Lacroix, C., et al, "Development of an innoviative and "green" stir bar sorptive extraction-thermal . . . ", Journal of Chromatography A, vol. 1349, (2014), pp. 1-10. Jan. 1, 2014.
Pintado-Herrera, Marina, et al, "Atmospheric pressue gas chromatography-time-of-flight-mass . . . stir bar sorptive extraction (SBSE)", Analytica Chimica Acta, vol. 851, (2014), pp. 1-13. Jan. 1, 2014.
Nallanthigal, Sridhara Chary, et al, "Determination of hormonally active chlorinated chemicals in waters at sub level using stir bar sorptive . . . ", International Journal of Environmental Analytical Chemistry, vol. 94, No. 1, (2016), pp. 48-64. Mar. 12, 2016.
Ochiai, Nobuo, et al, "Multi-stir bar sorptive extraction for analysis of odor compounds in aqueous samples", Journal of Chromatography A, vol. 1315, (2013), pp. 70-79. Sep. 20, 2013.
Assoumani, Azziz, et al, "In situ application of stir bar soprtive extraction as a passive sampling technique for the monitoring of agricultural pesticides in surface waters", Science of the Total Environment, vol. 463-464, (2013), pp. 829-835. Jun. 6, 2013.
Camino-Sanchez, F.J., et al, "Screening and Quantification of 65 Organic Pollutants in Drinking Water by Stir Bar Sorptive Extraction-Gas . . . ", Food Analytical Methods, vol. 6, (2012), pp. 854-867. Aug. 16, 2012.
Margoum, Christelle, et al, "Stir bar sorptive extraction coupled to liquid chromatography-tandem mass spectometry for the determination of pesticides in water . . . ", Talanta, vol. 116, (2013), pp. 1-7. Apr. 24, 2013.
Magi, Emanuele, et al, "Emerging pollutants in aquatic environments: monitoring of UV filters in urban wastewater treatment plants", Analytical Methods, vol. 5, (2012), pp. 428-433. Nov. 12, 2012.
Pintado-Herrera, Marina G., et al, "Environmentally friendly analysis of emerging contaminants by pressurized hot water extraction-stir bar sorptive extraction . . . ", Analytical Bioanal Chemistry, vol. 405, (2012), pp. 401-411. Sep. 21, 2012.
Camino-Sanchez, F.J., et al, "Validation of a method for the analysis of 77 priority persistent organic . . . ", Talanta, vol. 89, (2012), pp. 322-334. Dec. 4, 2011.
Tankiewicz, Maciej, et al, "Solventless and solvent-minimized sample preparation techniques for determining currently used pesticides in water samples: A Review", Talanta, vol. 86, (2011), pp. 8-22. Aug. 28, 2011.
Ochaia, Bobuo, et al, "Stir bar sorptive extraction and comprehensive two-dimensional gas . . . ", Journal of Chromatography A, vol. 1218, (2011), pp. 6851-6860. Aug. 4, 2011.
Rane, M.V., et al, "Heat pump operated freeze concentration system with tubular heat exchanger for seawater desalination", Energy for Sustainable Development, vol. 15, (2011), pp. 184-191. Mar. 6, 2011.

(56) References Cited

OTHER PUBLICATIONS

Shwartz, J., et al, "An analysis of counterwashers for freeze-distillation desalination", Desalination, vol. 4, Issue 1, (1968), pp. 5-29. Jan. 1, 1968.
Shwartz, Josef, et al, "Experimental Study of Slurry Separators for Use in Desalination", Desalination, vol. 6, (1969), pp. 239-266. Jan. 1, 1969.
Khawaji, Akili D., et al, "Advances in seawater desalination technologies", Desalination, vol. 221, (2008), pp. 47-69. Jan. 3, 2007.
Gao, W., et al, "Freeze concentration for removal of pharmaceutically active compounds in water", Desalination, vol. 249, (2009), pp. 398-402. Dec. 13, 2009.
Gao, W., et al, "Removal of organic contaminants and toxiciy from industrial effluents using freezing processes", Desalination, vol. 245, (2009), pp. 108-119. Jun. 27, 2008.
Shapiro, Joseph, "Freezing-Out, a Safe Technique for Concentration of Dilute Solutions", Science, vol. 133, No. 3470, (1961), pp. 2063-2064. Jun. 30, 1961.
Shapiro, Joseph, "Concentration of Volatile Substances in Aqueous Solution and Production of Water Free of Organics by Freezing Out", Analytical Chemistry, (1966), p. 280. Aug. 11, 1966.
Kammerer, Jr., Phil, et al, "Freeze Concentration of Organic Compounds in Dilute Aqueous Solutions", Environmental Science and Technology, vol. 3, No. 3, (1969), pp. 276-278. Mar. 1, 1969.
Baker, Robert A., "Trace Organic Contaminent Concentration by Freezing—II: Inorganic Aqueous Solutions", Water Research, vol. 1, (1967), pp. 97-113. Nov. 7, 1966.
Baker, Robert A., "Trace Organic Contaminant Concentration by Freezing—I. Low Inorganic Aqueous Solutions", Water Research, vol. 1, (1966), pp. 61-77. Sep. 9, 1966.
Baker, Robert A., "Microchemical Contaminants by Freeze Concentration and Gas Chromatography", Journal (Water Pollution Control Federation), vol. 37, No. 8, (Aug. 1965), pp. 1164-1170. Aug. 31, 1965.
Jaech, J.L., "Freeze-Concentation of Dilute Aqueous Solutions", Analytical Checmistry, vol. 36, No. 11, (1964), pp. 2197-2198. Oct. 31, 1964.
Kepner, Richard E., et al, "Freeze Concentration of Volatile Components in Dilute Aqueous Solutions", J. Agr. Food Chemistry, vol. 17, No. 5, (1969), pp. 1123-1127. Oct. 31, 1969.
Balazy, Michael, et al, "S-Nitroglutathione, a Product of the Reaction between Peroxynitrite and Glutathione that Generates Nitric Oxide", Journal of Biological Chemistry, vol. 273, No. 48, (1998), pp. 32009-32015. Nov. 27, 1998.
Van Hoeck, Els, et al, "Multiresidue screenign of endocrine-disrupting chemicals and pharmaceuticals in aqueous samples by multi-stir bar sorptive extraction . . . ", Analytical Bioanal Chemistry, vol. 393, (2009), pp. 907-919. Aug. 5, 2008.
Nogueira, J.M.F., "Novel sorption-based methodologies for static microextraction analysis: A review of SBSE and related techniques", Analytica Chimica Acta, vol. 757, (2012), pp. 1-10. Oct. 16, 2012.
Talebpour, Zahra, et al, "Methyl Methacrylate-Ethyleneglycol Dimethacrylate-Acrylic Acid Surface as Stationary Phase for Sitr Bar Sorptive Extraction", Chromatographia, vol. 72, No. 7/8, (2010), pp. 707-712. Jul. 12, 2010.
Yang, Lienqing, et al, "Selective enrichment and determination of nicosulfuron in water and soil by a stir bar based on molecularly imprinted polymer coatings", Analytica Chimica Acta, vol. 670, (2010), pp. 72-77. Apr. 25, 2010.
Zhu, Xiaolan, et al, "Molecular Imprinted Nylon-6 Stir Bar as a Novel Extraction Technique for Exantioseparation of Amino Acids", Journal of Applied Polymer Science, vol. 109, (2008), pp. 2665-2670. Sep. 27, 2007.
Zhu, Xiaolan, et al, "Films coated with molecular imprinted polymers for the selective stir bar sorptive extraction of monocrotophos", Journal of Chromatography A, vol. 1131, (2006), pp. 37-44. Jul. 18, 2006.
Jackson, Randy, et al, "Molecularly imprinted polymer stir bar sorption extraction and electrospray ionization tandem mass spectrometry for determination . . . ", Analytical Methods, vol. 2, (2010), pp. 552-557. Feb. 24, 2010.
Baskin, Steven I., et al, "Spectrophotometric Analysis of the Cyanide Metabolite 2-Aminothiazoline-4 Carboxylic Acid (ATCA)", Mechanisms and Methods, vol. 16, (2006), pp. 339-345. Jul. 13, 2005.
Bhandari, Raj K., et al, "Simultaneous high-performance liquid chromatography-tandem mass spectrometry (HPLC-MS) analysis of cyanide and thiocyanate from swine plasma", Analytical Bioanal Chemistry, vol. 406, (2014), pp. 727-734. Nov. 26, 2013.
Bhandari, Raj K., et al, Simultaneous determination of cyanide and thiocyanate in plasma by chemical ionization gas chromatography mass-spectrometry (CI-GC-MS), Analytical Bioanal Chemistry, vol. 404, (2012), pp. 2287-2294. Aug. 14, 2012.
Jackson, Randy K., et al, "Development of a Fluorescence-Based Sensor for Rapid Diagnosis of Cyanide Exposure", Analytical Chemistry, vol. 86, (2014), pp. 1845-1852. Jan. 3, 2014.
Logue, Brian A., et al, "Determination of the cyanide metabolite 2-aminothiazoline-4-carboxylic acid in urine and plasma by gas chromatography-mass spectrometry", Journal of Chromatography B, vol. 819, (2005), pp. 237-244. Jan. 10, 2005.
Mitchell, Brendan L., et al, "Rapid quantification of demethyl methylphosphonate from activated carbon particles by static headspace gas chromatography mass spectrometry", Journal of Chromatography A, vol. 1293, (2013), pp. 120-125. Mar. 12, 2013.
Mitchell, Brendan L., et al, "Quantification of x-ketoglutarate cyanohydrin in swine plasma by ultra-high performance liquid chromatography tandem mass spectrometry", Journal of Chromatography B, vol. 934, (2013), pp. 60-65. Jun. 27, 2013.
Stutelberg, Michael W., et al, "Determination of 3-mercaptopyruvate in rabbit plasma by high performance liquid chromatography tandem mass spectrometry", Journal of Chromatography B, vol. 949-950, (2014), pp. 94-98. Jan. 5, 2014.
Youso, Stephanie L., et al, "Determination of cyanide exposure by gas chromatography-mass spectrometry analysis of cyanide-exposed plasma proteins", Analytica Chimica Acta, vol. 677, (2010), pp. 24-28. Jan. 14, 2010.
Logue, Brian A., et al, "The Analysis of Cyanide and its Breakdown Products in Biological Samples", Critical Reviews in Analytical Chemistry, vol. 40, (2010), pp. 122-147. Jan. 1, 2010.
Youso, Stephanie L., et al, "The Analysis of Protein-Bound Thiocyanate in Plasma of Smokers and Non-Smokers as a Marker of Cyanide Exposure", Journal of Analytical Toxicology, vol. 36, (2012), pp. 265-269. Apr. 2, 2012.
Vinnakota, Chakravarthy V., et al, "Comparison of cyanide exposure markers in the biofluids of smokers and non-smokers", Biomarkers, vol. 17, No. 7, (2012), pp. 625-633. Jul. 4, 2012.
Petrikovics, Ilona, et al, "Organ-distribution of the metabolite 2-aminothiazoline-4-carboxylic acid in a rat model following cyanide exposure", Biomarkers, vol. 16, No. 8, (2011), pp. 686-690. Sep. 20, 2011.
Logue, Brian A., et al, "The analysis of 2-amino-2-thiazoline-4-carboxylic acid in the plasma of smokers and non-smokers", Toxicology Mechanisms and Methods, vol. 19, No. 3, (2009), pp. 202-208. Sep. 14, 2008.
Petrikovics, Ilona, et al, "Plasma persistence of 2-aminothiazoline-4-carboxylic acid in rat system determined by liquid chromatography tandem mass spectrometry", Journal of Chromatography B, vol. 891-892, (2012), pp. 81-84. Jan. 22, 2012.
Mitchell, Brendan L., et al, "Toxicokinetic profiles of x-ketoglurarate cyanoydrin, a cyanide detoxification product, following exposure to potassium cyanide", Toxicology Letters, vol. 222, (2013), pp. 83-89. Jul. 7, 2013.
Bhandari, Raj K., et al, "Cyanide Toxicokinetics: The Behavior of Cyanide, Thiocyanate and 2-Amino-2-Thiazoline-4-Carboxylic Acid in Mulitple Animal Models", Journal of Analytical Toxicology, vol. 38, (2014), pp. 218-225. Jan. 1, 2014.
Logue, Brian A., et al, "Role of Surface Altercation in Determining the Mobility of U(VI) in the Presence of Citrate: Implications for Extraction of U(VI) from Soils", Envrionmental Science Technology, vol. 38, (2004), pp. 3752-3759. Apr. 27, 2004.

(56) References Cited

OTHER PUBLICATIONS

Logue, Brian A., et al, "U(VI) adsorption on natural iron-coated sands: comparison of approaches for modeling adsorption on heterogeneous environmental materials", Applied Geochemistry, vol. 19, (2004), pp. 1937-1951. May 26, 2004.

Logue, Brian A., et al, "Kinetics of Reduction of Nitrobenzene and Carbon Tetrachloride at an Iron-Oxide Coated Gold Electrode", Environmental Science Technology, vol. 37, No. 11, (2003), pp. 2356-2362. Apr. 30, 2003.

Gu, X., et al, "Limiting Partition Coefficient in Progressive Freeze-concentration", Journal of Food Science, vol. 70, No. 9, (2005), 6 pages. Nov. 21, 2005.

Fialkov, Alexander B., et al, "Sensitivity and noise in GC-MS: Achieving low limits of detection for difficult analytes", International Journal of Mass Spectrometry, vol. 260, (2007), pp. 31-48. Apr. 3, 2006.

United States Environmental Protection Agency, "Table of Regulated Drinking Water Contaminants", United States Environmental Protection Agency, (2016), 11 pages, last accessed Mar. 3, 2016. Mar. 3, 2016.

European Patent Office, "Extended European Search Report", issued in connection to European Application No. 16195607.3, dated Mar. 23, 2017, 10 pages.

Serodio, P., et al., "Considerations on ultra-trace analysis of phthalates in drinking water", Water Research, Elsevier, Amsterdam, NL, vol. 40, No. 13, Jul. 1, 2006, pp. 2572-2582, XP027902264, ISSN: 0043-1354.

Namiesnik, J, et al., "Isolation and preconcentration of volatile organic compounds from water", Analytica Chimica Acta, Elsevier, Amsterdam, NL, vol. 237, Jan. 1, 1990, pp. 1-60, XP026724549, ISSN: 0003-2670.

Maslamani Nujud et al., "Ice Concentration Linked with Extractive Stirrer (Icecles)", Analytica Chimica Acta, Elsevier, Amsterdam, NL, vol. 941, Sep. 9, 2016, pp. 41-48, XP029751872, ISSN: 0003-2670.

Yonehara, Norinobu et al, "Freeze Concentration of Dilute Aqueous Solution", Department of Chemistry, Faculty of Science, Kagoshima University, 1-21-35, Korimoto, Kagoshima-shi, Kago-Shima. Aug. 12, 1976.

\* cited by examiner

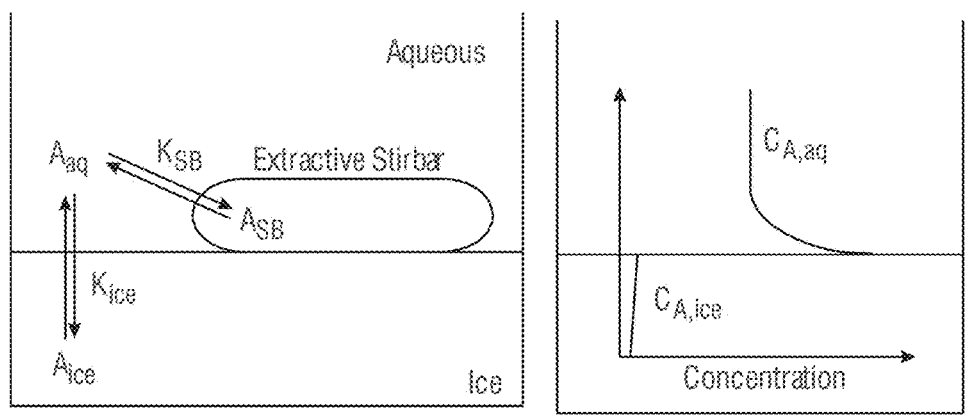
*FIG. 4A*  *FIG. 4B*

SBSE

ICECLES

METHODS AND APPARATUSES FOR TRACE AND ULTRATRACE ANALYSIS

FIELD OF THE INVENTION

The invention relates to selective trace and ultratrace analysis of analytes. In particular, this analysis is achieved by simultaneously freeze concentrating and extracting the analyte into a sorptive or by a sorptive material. Further, the methods and apparatus of the present invention can be useful in conducting ultratrace analysis for toxic chemicals that may be present in drinking water. Further, the methods and apparatus of the present invention can be useful in concentrating and isolating target chemicals of high value.

BACKGROUND OF THE INVENTION

Analytical chemistry is concerned with both identification and quantification of chemicals. Trace and ultratrace analysis is focused on miniscule quantities. Trace and ultratrace analysis can be important in many areas of analytical chemistry. For example, it can be useful in forensic analysis, quality control, and the analysis of toxins. Sample preparation, including preconcentration, is a key step for almost all analyses. Sample preparation and preconcentration, along with highly sophisticated instrumentation becomes increasingly important when trace and ultratrace detection of analytes is necessary. In addition to more historic sample preparation techniques such as liquid-liquid extraction and simple solvent evaporation, multiple techniques have been introduced over the past several decades to aid analysts in determined low concentrations of analytes such as solid-phase extraction (SPE), solid-phase microextraction (SPME), and stir bar sorptive extraction (SBSE). While the compatibility of each analyte with these techniques must be individually evaluated, these sample preparation techniques have generally produced decreased limits of detection, decreased analysis times, and decreased organic solvent use. Although current sample preparation techniques are excellent for analysis in the parts-per-billion (ppb; µg/L) and high parts-per-trillion (ppt; ng/L) range, ultratrace analysis is still very difficult for analytical chemists to achieve without arduous sample preparation and/or extremely sophisticated and expensive instrumentation. In some cases, even with the most sensitive instruments, analysis of a compound of interest at a desired concentration may still not be possible without concentrating large sample volumes (e.g., greater than 500 mL). Therefore a technique with the ability to more easily determine ultratrace concentrations of interest could be a foundational technique in the field of analytical sample preparation. Furthermore, such a technique would allow more applicable standards to be set of toxic compounds of interest and help ensure human health, to include safe drinking water standards.

The ability to analyze contaminants at ultratrace concentrations is a critically important, but currently challenging, aspect of ensuring safe drinking water. The EPA Maximum Contaminant Level Goal (MCLG) is zero for several compounds, but the enforceable contaminant level, called the Maximum Contaminant Level (MCL), is set, in part, according to the ability of laboratories to measure accurately and consistently the level of the contaminant with available analytical methods. This typically limits MCLs to the parts-per-billion or microgram per liter range. The ability to more easily analyze compounds at extremely low concentrations would be a tremendous achievement in the analytical chemistry field and would have a broad impact, including, for example, in assisting with the provision of safe drinking water. The present invention allows analysis of select compounds in liquid solution at much lower limits-of-detection (LODs) than currently available. In the absence of the present invention, performing trace and ultratrace analysis of certain classes of solutes in drinking water samples, and ultimately ensuring safe drinking water, will remain difficult and force undesirable analytical alternatives (e.g., expensive instrumentation and/or concentrating large sample volumes).

In the past several decades, multiple sample preparation techniques have been introduced to extend the reach of analytical methods into the low parts-per-billion, parts-per-trillion, and even parts-per-quadrillion range by purifying and pre-concentrating target analytes and using sophisticated instrumentation. Sample preparation techniques such as SPE, SPME, and SBSE can extend the concentration range for analysis to ultratrace levels. Although these sample preparation techniques may work well for certain analytes, each has disadvantages, such as limited preconcentration factors among others. For example, SBSE has limitations on the type of analytes for which the procedure can be used due to the limited number of sorbent phases available. Further, SPE typically has a need for a drying step prior to analysis.

Further, although freeze concentration (FC) has received little attention the field of analytical chemistry, it has been used for decades to concentrate solutes from solutions and has found common application in the food industry for creating frozen concentrates of fruit juices and ice beer. As the name implies, FC is a technique for concentrating solutes by freezing a solution. Solutes are concentrated based on the direct relationship between freezing point depression and solute molality. If a solution is slowly frozen, local regions of solvent with a low solute concentration are frozen first and the solution left behind is more concentrated. Although higher solute concentrations decrease the freezing point of a solution, the rate of freezing is generally too fast to freeze out pure solvent when high solute concentrations are present. Therefore, the solution is typically stirred vigorously during FC to counteract incorporation of the solute into the frozen solvent. However, FC is indiscriminant as to the solutes that are concentrated.

Accordingly, it is an objective of the claimed invention to develop a method and apparatus of selective preconcentration and isolation which can discriminate particular compounds. The method and apparatus may be used to facilitate trace and ultratrace analysis or isolation of high value compounds.

A further object of the invention is to allow the trace and ultratrace analysis of toxic chemicals which currently cannot be easily analyzed at the desired concentrations (e.g., maximum contaminant levels; MCLs).

BRIEF SUMMARY OF THE INVENTION

The invention provides apparatuses and methods for performing trace and ultratrace analysis by simultaneously freeze concentrating and extracting the analyte into or by a sorptive material. The analyte can be extracted from the sorptive material, identified by qualitative analysis, and/or quantified by quantitative analysis. In a preferred embodiment, the apparatuses and methods of the invention can be applied to the monitoring of drinking water.

An advantage of the invention is that it provides apparatuses and methods that can be applied to very low concentrations of analyte in a liquid medium.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 4A shows that there are three material phases with which the analyte while associated in the present invention: liquid, solid, and stir bar. FIG. 4B shows the concentration profile of the analyte near the ice-liquid interface.

FIG. 17A shows the limit of detection of benzyl alcohol using the present invention while

Figure 1:
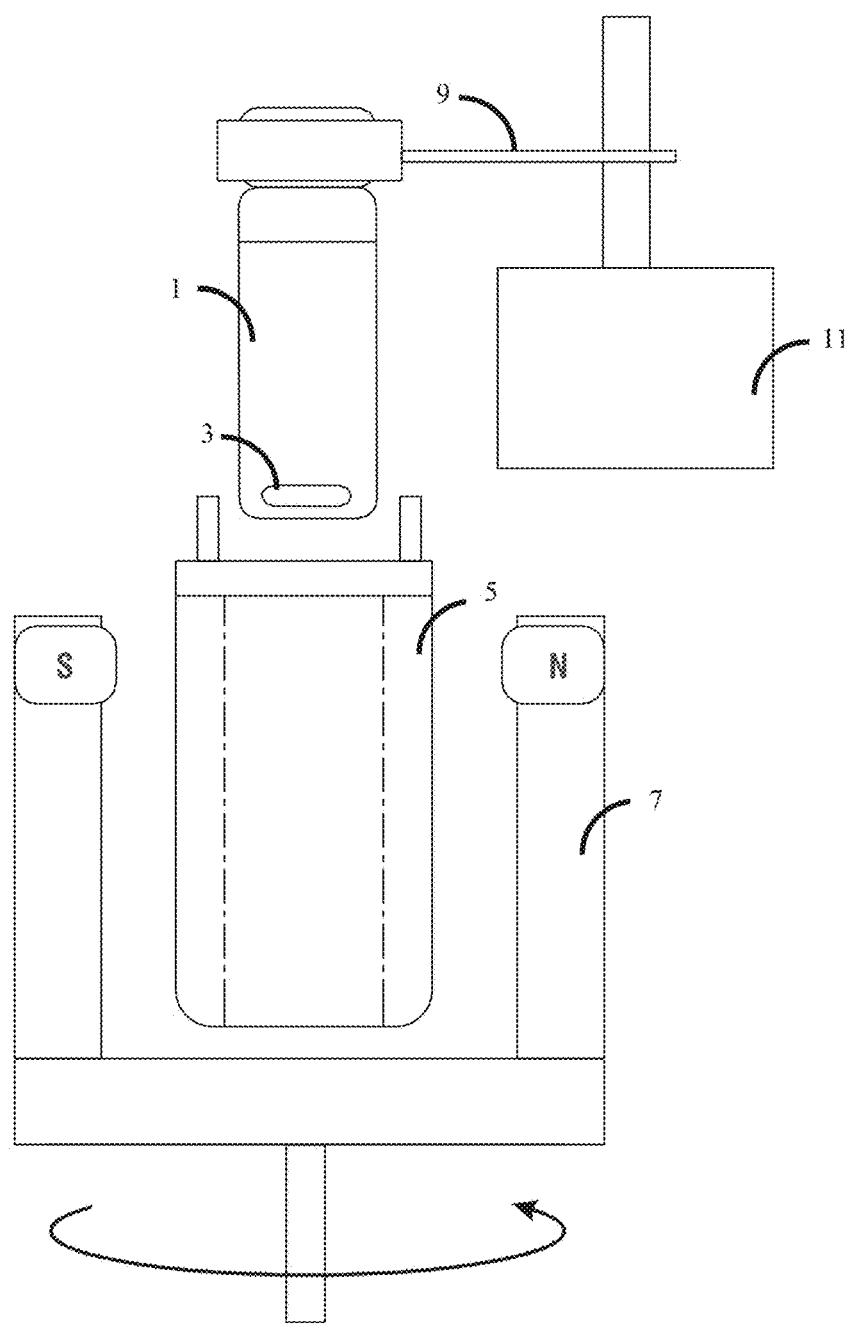
FIG. 1 illustrates an apparatus of the present invention including a u-shaped bracket.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present invention relates selective concentration of solutes for trace and ultratrace analysis. The methods and apparatus of the present invention have many advantages over existing trace and ultratrace analyses. For example, the present invention increases the concentration factor (i.e., the ratio of the concentration of analyte in the prepared sample to that in the original solution) of selected solutes over existing sample preparation methods.

The embodiments of this invention are not limited to particular apparatuses for performing the methods of invention, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range (e.g., 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "analyte," as used herein, is a substance whose chemical constitutes are being identified and measured. "Solute," as used herein, is the minor component in a solution, dissolved in the solvent. Further, analyte may be used interchangeably with solute.

The term "ICELES" as used herein, is an abbreviation for "ice concentration extraction linked with extractive stirring," which can be used to describe an exemplary method of the invention.

The term "$K_{solid}$," as used herein, refers to the effective partitioning constant between the solid and the liquid phase. Additionally, log $K_{solid}$ is defined as the log value of $K_{solid}$.

The term "$K_{ow}$," as used herein, refers to the octanol-water partition coefficient, or the ratio of the solubility of a compound in octanol to its solubility in water. The higher the $K_{ow}$, the more non-polar the compound. Additionally, log $K_{ow}$ is defined as the log value of $K_{ow}$.

The term "$K_{SB}$," as used herein, refers to the effective partitioning coefficient between the stir bar and the liquid phase. Additionally, log $K_{sb}$ is defined as the log value of $K_{sb}$.

The term "limit of blank" or "LOB," as used herein is highest apparent analyte concentration expected to be found when replicates of a blank sample containing no analyte are tested.

The term "limit of detection" of "LOD," as used herein is the lowest analyte concentration likely to be reliably distinguished from the LOB and at which detection is feasible.

The term "lower limit of quantification" or "LLOQ," as used herein, is the lowest concentration at which the analyte can not only be reliably detected but at which some pre-defined goals for bias and imprecision are met.

The term "parts-per-billion" or "ppb," as used herein is one part per 1,000,000,000 parts and corresponds to 1 μg/L with a density of water of 1.0 g/mL. Similarly, "parts-pertrillion" or "ppt," as used herein in one part per 1,000,000,000,000 and corresponds to 1 ng/L with a density of water of 1.0 g/mL.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods, systems, apparatuses, and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

Apparatuses

Embodiments of the invention include methods and apparatuses for selective trace and ultratrace analysis. The methods and apparatuses according to the invention are capable of concentrating analytes from a sample for analysis at trace and ultratrace levels. The invention overcomes the shortfalls of conventional trace and ultratrace analysis techniques by reducing the sample volume while permitting trace and ultratrace analysis. Additionally, the invention is capable of targeting desired analytes.

The apparatuses for performing trace and ultratrace analysis can include a vial or other suitable container, sorptive stirrer, and cooling source. In some aspects the apparatus further includes a magnet. In some aspects the apparatus further consists of a stir plate. In some aspects the apparatus may include an overhead stirrer. In some aspects, the apparatus may optionally include at least one measurement device. In some aspects the apparatus may optionally include a control system.

The apparatus includes a container in which the sample to be analyzed is placed. Any suitable container for holding the sample that will permit the rotation of a sorptive stirrer can be used including, for example, but not limited to, a beaker, flask, test tube, or vial. The container can be supported on its own or by any suitable support, including, for example a test tube or vial holder, a clamp, a bracket, or an arm.

The apparatuses and methods of the invention employ a sorptive stirrer comprising a sorptive material. The analyte can be absorbed into or adsorbed by the sorptive material. The sorptive material can be a coating, a jacket, or a layer on a stirrer. In some embodiments the sorptive stirrer can have a layer, jacket, or coating that is chemically-inert, or sufficiently inert so as not to impact the analyte's adsorption by or absorption into the sorptive material. A preferred chemically-inert coating, layer, or jacket is glass. Other suitable chemically-inert coating, layers, or jackets can be used.

In some embodiments of the invention, the sorptive stirrer is a magnetic stir bar with a sorptive jacket or sorptive layer is contained within the vial. In some embodiments the sorptive stirrer is an overhead stirrer with sorptive jacket or sorptive layer can be used. Preferably, the magnetic stir bar with sorptive jacket/layer is a magnetic bar contained within a sealed glass container which is fitted or coated with a sorptive layer. Preferably, an overhead stirrer with sorptive jacket/layer is an overhead stirrer with a stir rod that can be inserted into the sample container which is coated or fitted with sorptive material such that the sorptive material is immersed in the sample within the container.

The sorptive material can be selected to target specific analytes. In an embodiment of the invention, the sorptive material can include, but is not limited to, polydimethylsiloxane, polydimethylsiloxane/ethylene glycol copolymer, molecularly imprinted polymers, ion exchange material, or other common sorbent phases. In a preferred embodiment, the sorptive layer is polydimethylsiloxane.

The apparatus also includes one or more magnets for stirring the stir bar. A magnet can be part of a stir plate, U-shaped bracket having magnets in each arm, or donut-shaped ring having magnets housed in the ring on opposite sides. Further, a magnetic field may be generated by electric current through an appropriate electric circuit. In embodiments using a U-shaped bracket, the vial and optionally the cooling source can be between the bracket arms and as the bracket rotates it causes the stir bar to spin. In embodiments using a donut-shaped ring, the vial is housed in the hole in the ring and as the ring is rotated, it causes the stir bar to spin. In embodiments with electric current generated magnetic fields, the vial is housed such that the magnetic fields rotate the stir bar within the container.

The apparatus can include a cooling source in order to freeze the sample. A cold bath is preferred cooling source. However, any suitable cooling source can be used to freeze the sample, including for example use of a jacketed beaker (i.e. a double-walled beaker with inlet and outlet to allow coolant flow), coolant, cooled air system, thermoelectric device, helium, or nitrogen system.

In some embodiments of the invention, the container is held by a holder that is connected to a stepper motor that lowers the container within the holder into the cooling source, such as a cold bath. The stepper motor is directed by a control system to maintain a given rate of descent of the container into the cooling source.

In some embodiments of the invention, the apparatus may include at least one measurement device or a plurality of measurement devices. Such measurement devices are those suitable to measure one or more variables of the system such as temperature, speed, pH, and combinations thereof. Such a measurement device can measure the cooling source, the container, magnetic field (e.g., strength and/or position), spectroscopic behavior of the analyte, the sorptive stirrer, etc. For example, in an embodiment of the invention, temperature is monitored at various points in the apparatus to ensure consistent freezing of the sample. In further aspects of the invention, the apparatus comprises an optional controller or software platform. The software platform provides a user or system to select speed and temperature of freezing as well as speed of stirring. As a result, use of the apparatus provides significant use flexibility to concentrate a variety of analytes for particular user-identified purposes. For example, the controller or control software for operation of the apparatus may permit a user or system to select both the temperature of the system and the speed of stirring. In a further aspect, the control software may determine the timing of the lowering of the vial and the overall concentration process. In a still further aspect of the invention, the control system includes the above described measurement devices.

In some embodiments of the invention, the entire apparatus or select components of the apparatus may be contained in a cooled container to control the temperature of the apparatus and sample.

According to an embodiment of the invention shown in the exemplary and non-limiting FIG. 1, the sample container 1 containing the sample and the sorptive stirrer 3, is lowered into a cooling source 5 which is surrounded by a magnet 7. Further the sample container is held by a sample holder 9 which can be lowered incrementally by a motor 11.

Figure 2:
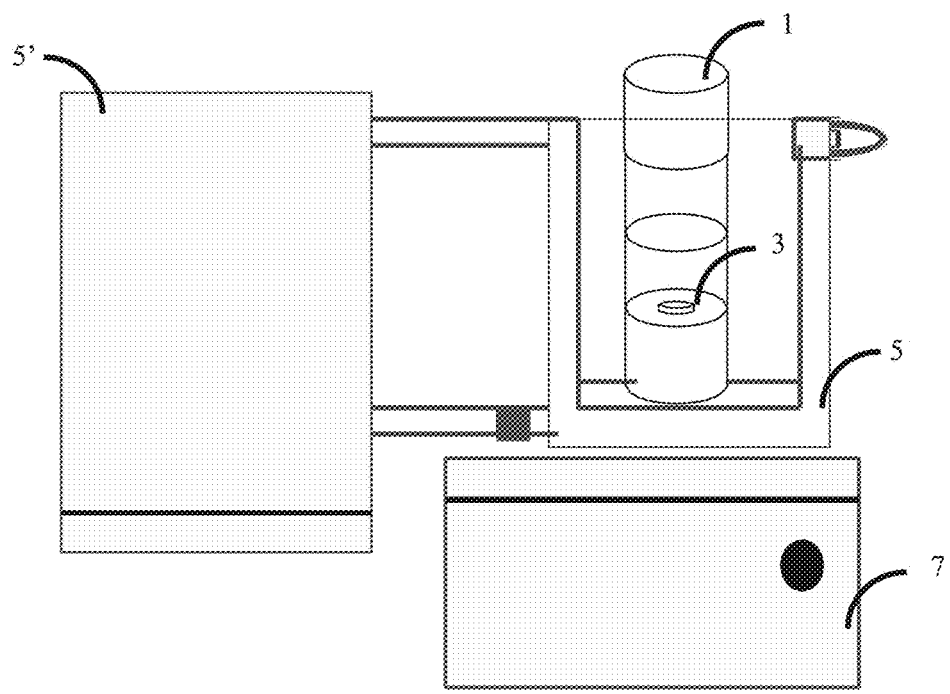
FIG. 2 illustrates an apparatus of the present invention including a magnetic stir plate.

According to an embodiment of the invention shown in the exemplary and non-limiting FIG. 2, the sample container 1 containing the sample and the sorptive stirrer 3, is lowered into a cooling source 5, 5', which is located on top of a magnetic stir plate 7.

Methods

The methods according to the present invention for conducting trace and ultratrace analysis of an analyte or concentrating a solute in a solvent can include providing an analyte for analysis, stirring the analyte and simultaneously cooling the analyte. The simultaneous cooling and stirring of the composition allows the solvent to freeze and solutes to become concentrated. According to the present invention, the analyte contained in a liquid medium is placed in the container along with the sorptive stirrer compatible with the analyte(s) of interest. Sorptive stirrer comprises a sorptive material. The analyte can be absorbed into or adsorbed by the sorptive material. In some embodiments, a step can be added to coat the stirrer with the sorptive material.

As the container is lowered into the cooling source, or alternatively as the solvent reaches its freezing point, the solvent begins to crystalize on the bottom of the container in an upward direction (relative to the bottom of the container) and the sorptive stirrer continues to stir on top of the frozen solvent. Once the solvent is completely frozen, the sorptive stirrer is removed from the top of the frozen solvent and can be analyzed by an analytical technique, such as gas-chromatography mass-spectroscopy (GCMS), thermal desorption GCMS, liquid chromatography, fluorometry, spectroscopy, or any other analytical technique. The analysis can include extraction of the analyte from the sorptive material. Preferably the extraction of the analyte is into a liquid solvent or into the gas phase such that it is amenable for follow-on analysis. Subsequent analytical techniques can be selected and applied to the analyte in a liquid, solid, and/or gas phase.

Figure 3:
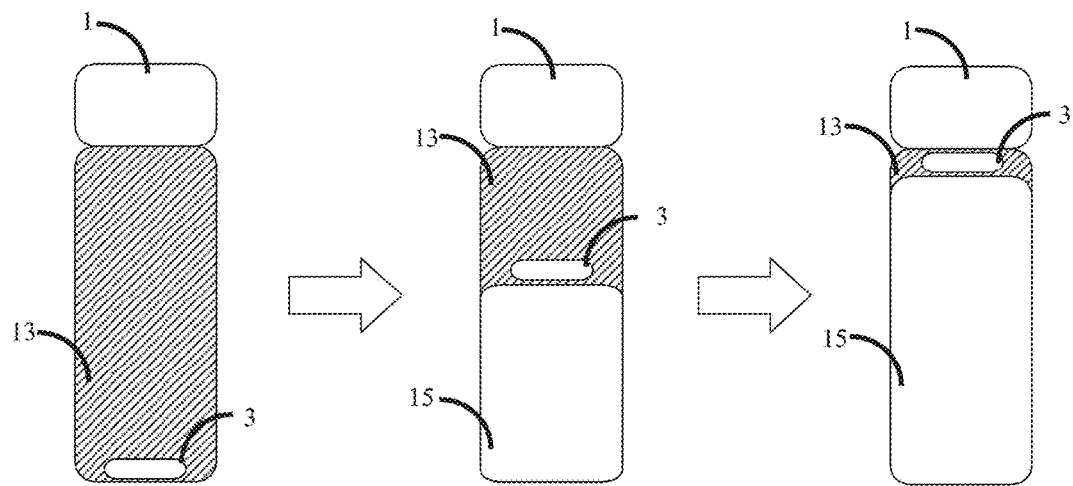
FIG. 3 illustrates the method and the different stages of concentration as they occur during the course of the method.

According to an embodiment of the invention shown in the exemplary and non-limiting FIG. 3, the method and the different stages of concentration as they occur during the course of the method are shown. The sample container 1 containing the liquid phase sample 13 and the sorptive stirrer 3 is cooled so that the crystalline phase 15 forms during the method.

While an understanding of the mechanism is not necessary to practice the present invention and while the present invention is not limited to any particular mechanism of action, it is contemplated that, in some embodiments, there are three material phases to consider: liquid, solid, and sorptive stirrer as shown in FIG. 4A. Some among of analyte (A) will be associated with each of these phases as shown in FIG. 4A. FIG. 4B shows the concentration profile of the analyte near the ice-liquid interface. Even though the analyte contained within the solid phase is not truly in equilibrium with other material phases in the system, the distribution of the analyte between the solid and liquid solution is described by an effective partition coefficient, $K_{solid}$. According the present invention, the effectiveness of the method for purposes of analytical sample preparation is indicated by the fraction of analyte extracted ($f_{extr,SB}$). For the present invention, the extracted analyte is analyzed from the sorptive stirrer. Equation 1 defines the fraction of the analyte extracted:

$$f_{extr,SB} = \frac{mol_{A,SB}}{mol_{A,SB} + mol_{A,solid} + mol_{A,l}} \quad (1)$$

where $mol_{A,SB}$, $mol_{A,solid}$, $mol_{A,l}$ are the amounts of analyte in the sorptive stirrer, solid, and liquid solution, respectively. Since the concentration of an analyte in any phase can be expressed as the amount of the substance (mol) per unit volume (L), Equation 1 can be written as Equation 2:

$$f_{extr,SB} = \frac{C_{A,SB}V_{SB}}{C_{A,SB}V_{SB} + C_{A,solid}V_{solid} + C_{A,l}V_l} \quad (2)$$

Where $C_{A,SB}$, $C_{A,solid}$, and $C_{A,l}$ represents the concentration of the analyte in the sorptive stirrer, solid, and liquid solution, respectively. $V_{SB}$, $V_{solid}$, and $V_l$ are the volume of the sorptive stirrer, solid, and liquid solution, respectively. If the distribution of the analyte is presumed to be in equilibrium, Equation 2 can be simplified to Equation 3:

$$f_{extr,SB} = \frac{K_{SB}V_{SB}}{K_{SB}V_{SB} + K_{solid}V_{solid} + V_l} \quad (3)$$

During the methods of the present invention, the volume of solid ($V_{solid}$) increases and the liquid volume ($V_l$) decreases until $V_l$ becomes negligible. Therefore, the equation describing the fraction of the analyte extracted into the stir bar becomes Equation 4:

$$f_{extr,SB} = \frac{K_{SB}V_{SB}}{K_{SB}V_{SB} + K_{solid}V_{solid}} \quad (4)$$

Since $K_{SB}V_{SB}$ must be much greater than $K_{solid}V_{solid}$ for an effective extraction to occur, wherein the fraction of analyte extracted approaches 1, and since the volume of the sorptive stirrer ($V_{SB}$) is small compared to the solid volume ($V_{solid}$), the $K_{SB}$ must be much greater than $K_{solid}$ for efficient extraction to occur according to the present invention.

Figure 5A:
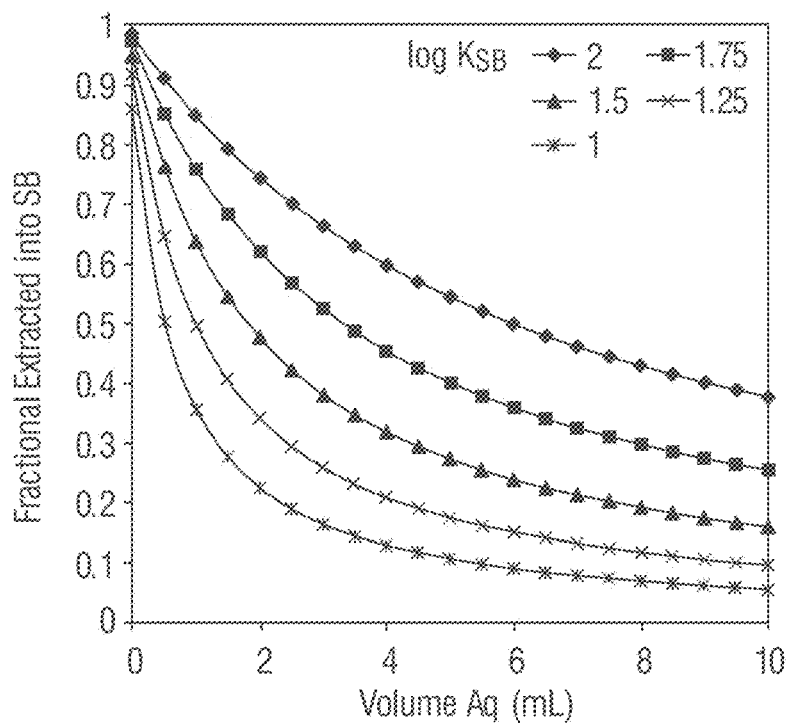
FIG. 5A illustrates the behavior of an analyte (i.e., the fraction of analyte extracted into the stir bar) as the analyte undergoes the methods of the present invention.
Figure 5B:
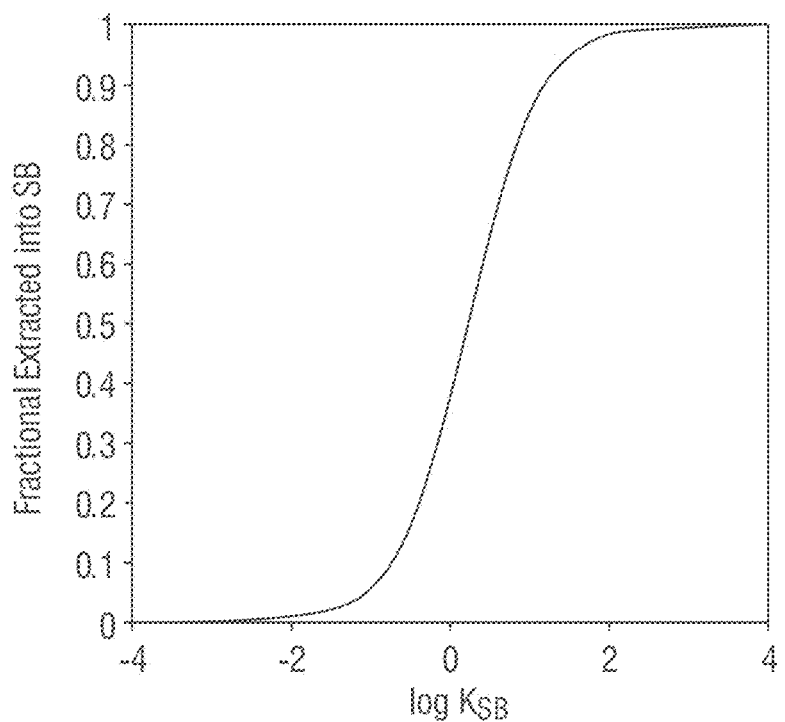
FIG. 5B indicates the fraction extracted into the stir bar as the $K_{SB}$ of the analyte increases.
Figure 5C:
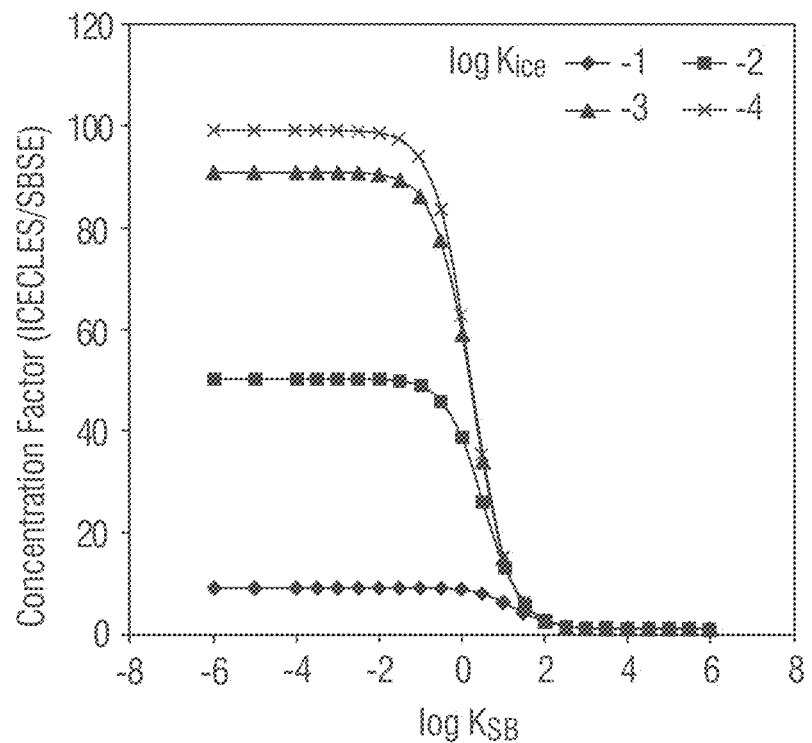
FIG. 5C shows that the present invention is advantageous for analysis over SBSE.

According to some embodiments of the invention, the log $K_{SB}$ is between −0.7 and 4.0; more preferably between −0.6 and 3.0; most preferably between −0.5 and 2.5. According to a further embodiment of the invention, for water as a solvent, $K_{solid}$ is generally on the order of 0.1 to 0.0001 ($pK_{solid}$ of 1 to 4) depending on the solvent, stir rate, solute concentration, and freeze rate. Without seeking to be limited to a particular theory, it is believed that because $K_{solid}$ decreases as the solute concentrations decreases, a $K_{solid}$ of approximately 0.01 is considered conservative for the analysis according to the present invention. Thus, preferably the invention extracts at least 80% of the analyte, more preferably at least 85% of the analyte, more preferably at least 90% of the analyte for those analytes with a $K_{SB}$ greater than 15. By comparison, this presents a significant advantage over the conventional methods of stir bar sorptive extraction. FIG. 5A illustrates the behavior of an analyte (i.e., the fraction of analyte extracted into the sorptive stirrer) as the analyte undergoes the methods of the present invention. As shown in FIG. 5A, for analytes with smaller $K_{SB}$, concentration into the stir bar is more pronounced over the last few mL of freezing and analytes with $K_{SB}$s that are typically too low for stir bar sorptive extraction are able to be extracted into the sorptive stirrer at over 80%. FIG. 5B indicates the fraction extracted into the sorptive stirrer as the $K_{SB}$ of the analyte increases. Using a $K_{solid}$ of 0.01, the fraction extracted rises to above 90% as the log $K_{SB}$ of the analyte increases to just over 1, whereas a log $K_{SB}$>3 is necessary to extract over 90% of the analyte under the same conditions. FIG. 5C shows that the present invention is advantageous for analysis over SBSE.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Figure 6C:
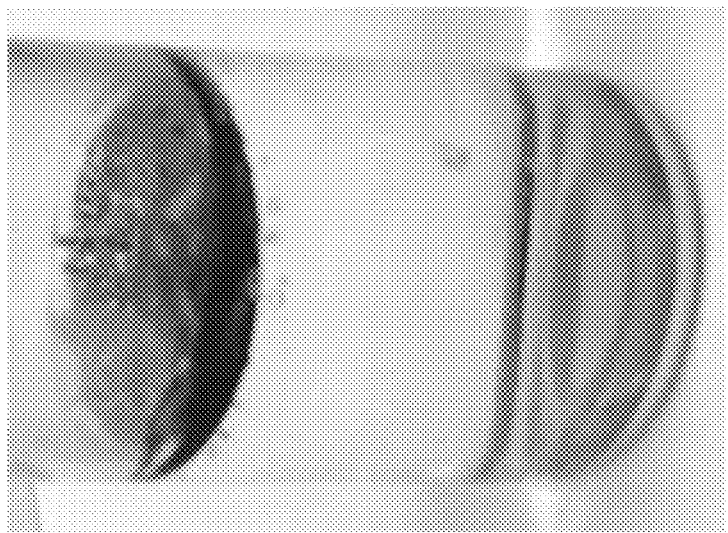
FIGS. 6A-C are photographs showing the concentration of the methyl violet at various points during Example 1.
Figure 6B:
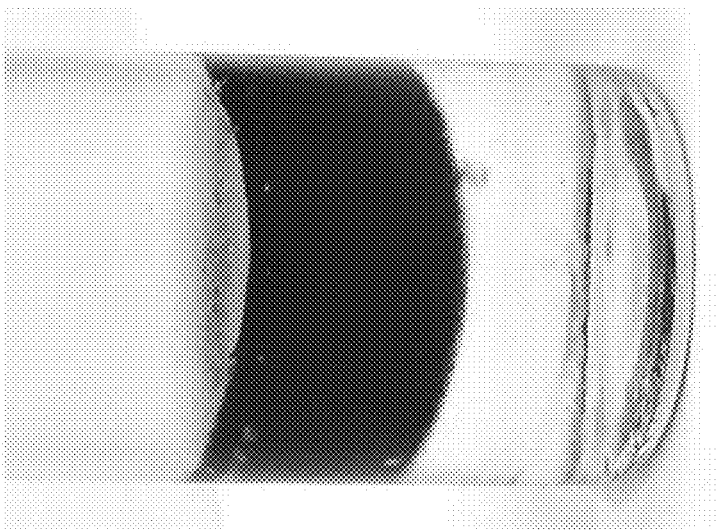
Figure 6A:
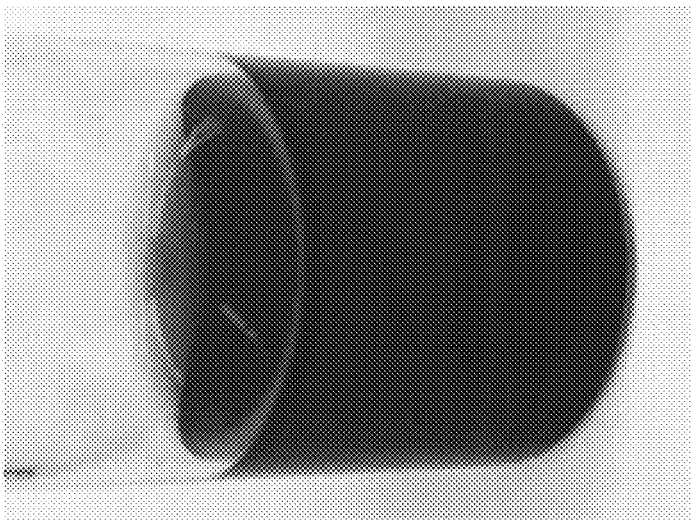

A dye solution was tested according to the methods and apparatus of the invention. The aqueous dye solution in the amount of 10 mL was placed in a vial with a sorptive stir bar. The vial was then placed into a jacketed beaker (i.e. a double-walled beaker with inlet and outlet to allow coolant flow). The concentration of methyl violet into the stir bar was visually confirmed. FIG. 6 is a series of photographs showing the concentration of the methyl violet at various points during the test. In FIG. 6A, the dye solution is visible prior to application of the methods of the invention. FIG. 6B shows the dye visibly separated on top of the crystalline phase during of the method, where approximately 50% of the dye solution has been frozen. FIG. 6C shows the dye solution visibly separated on top of the crystalline phase during the methods, where the dye has been concentrated and the majority of the water has been separated and frozen.

Example 2

Figure 7:
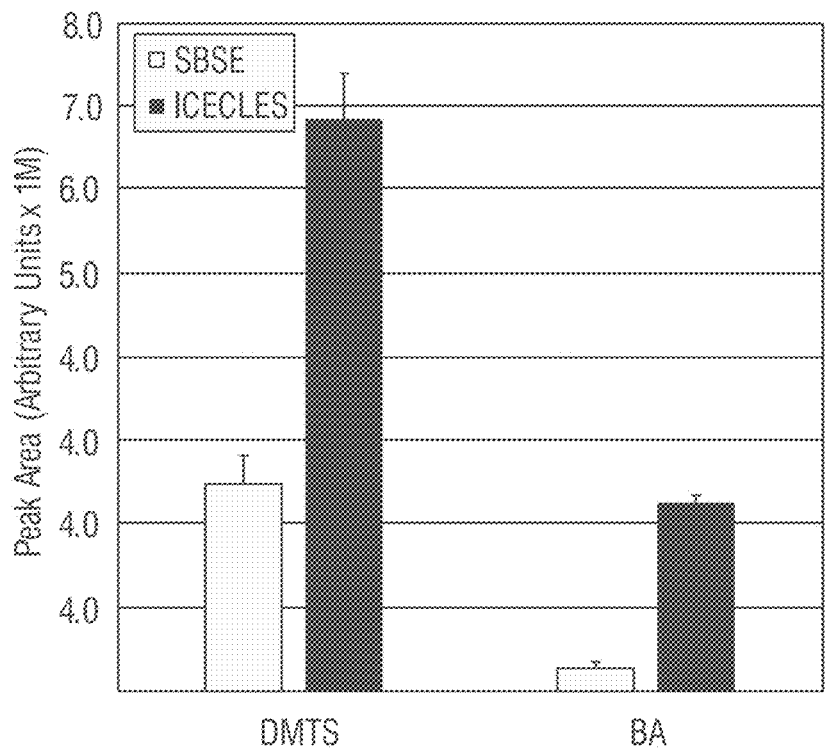
FIG. 7 indicates the results of the analysis based on peak area that the signs of both chemicals where enhanced by using the methods of the present invention.
Figure 8:
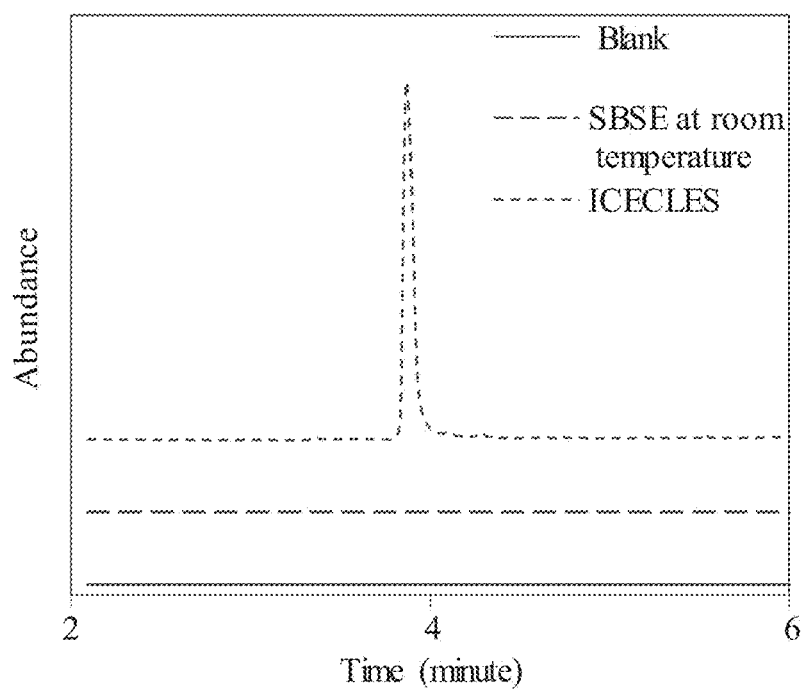
FIG. 8 shows the comparative peaks for SBSE and the present invention.
Figure 9:
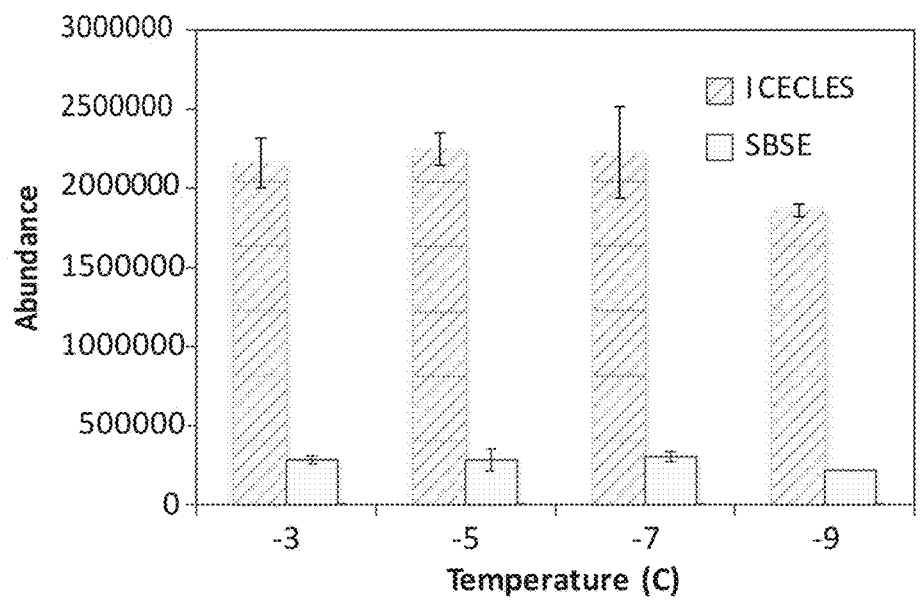
FIG. 9 indicates the concentration factors as a function of temperature for benzaldehyde.
Figure 10:
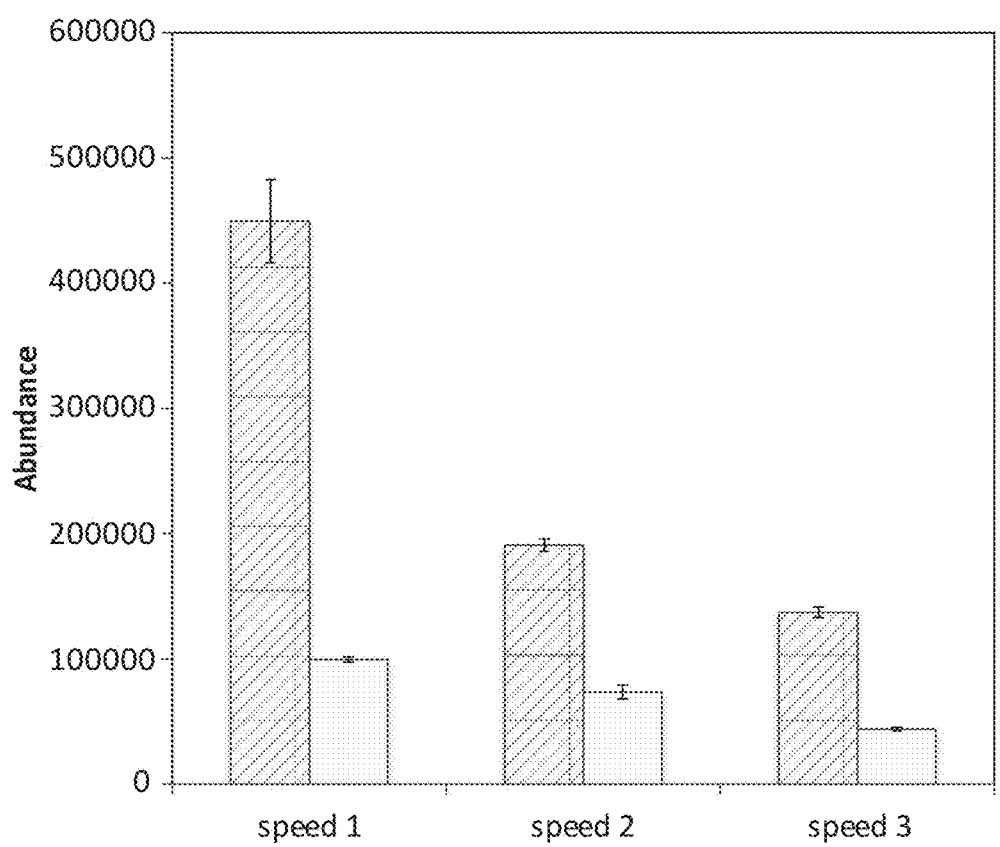
FIG. 10 indicates that concentration factors decreased with the increase of stir speed.
Figure 11:
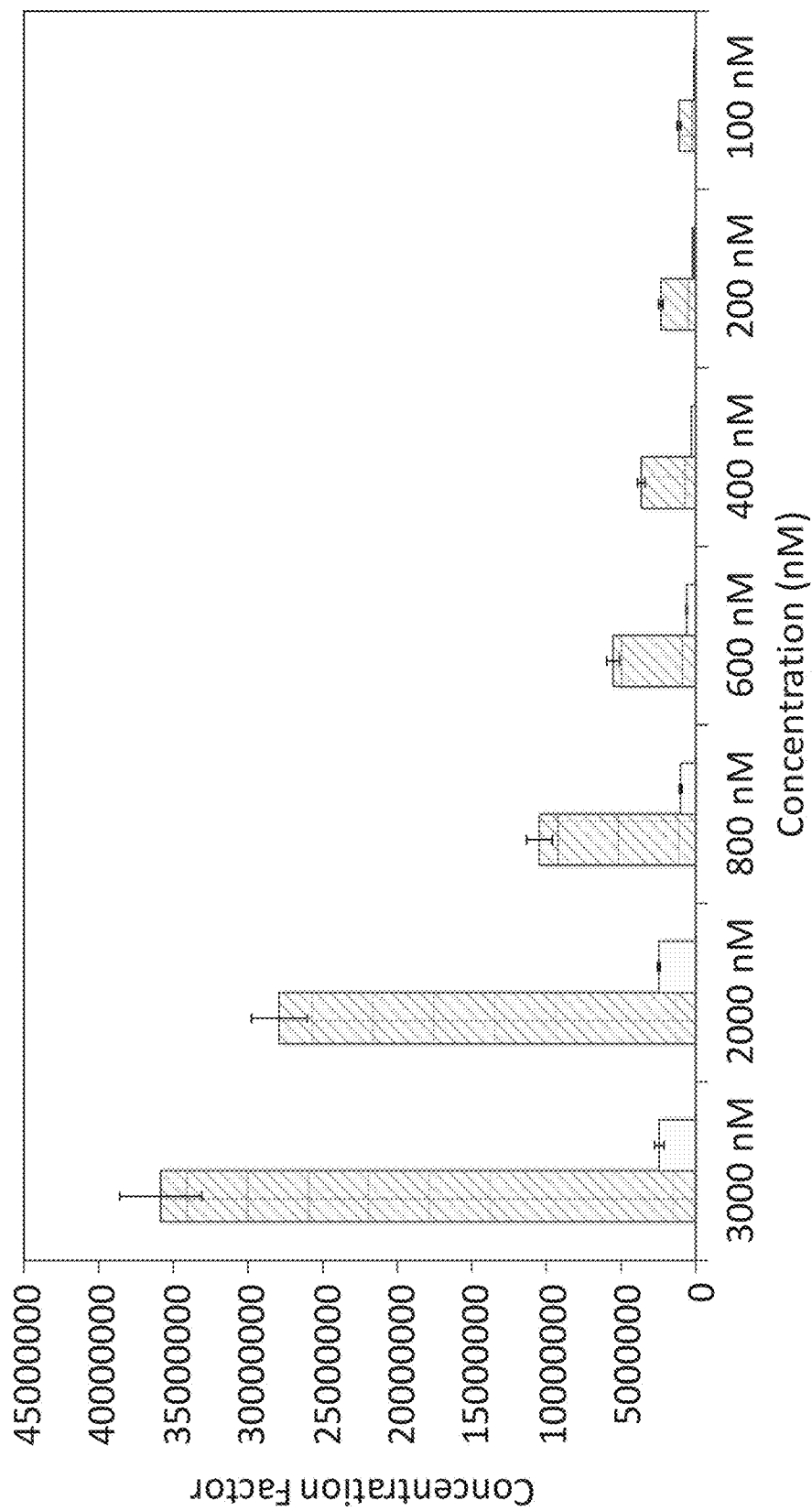
FIG. 11 illustrates the relationship between concentration and concentration factor.
Figure 12:
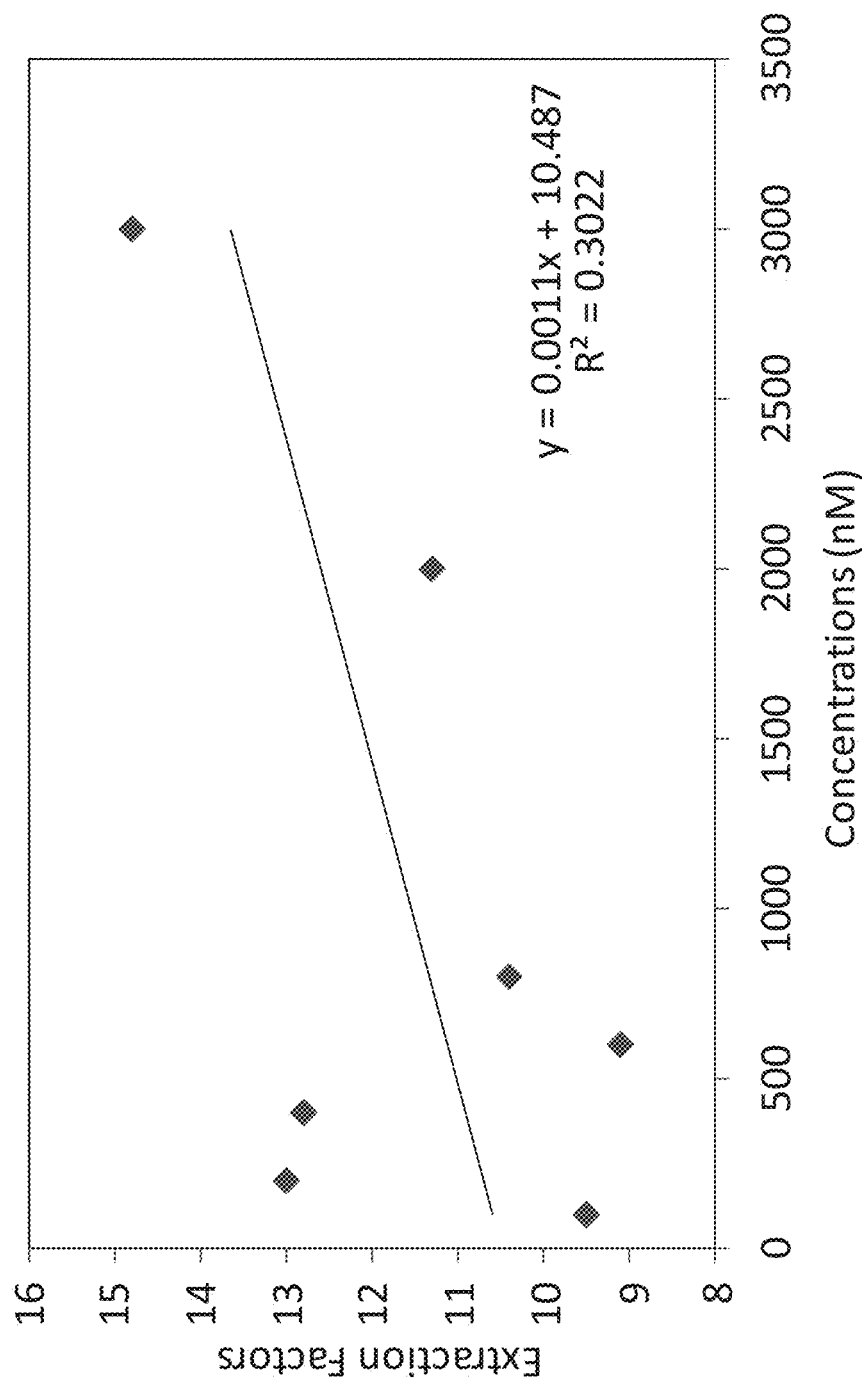
FIG. 12 indicates there is little to no correlation between the concentration factor and the solution concentration.
Figure 13A:
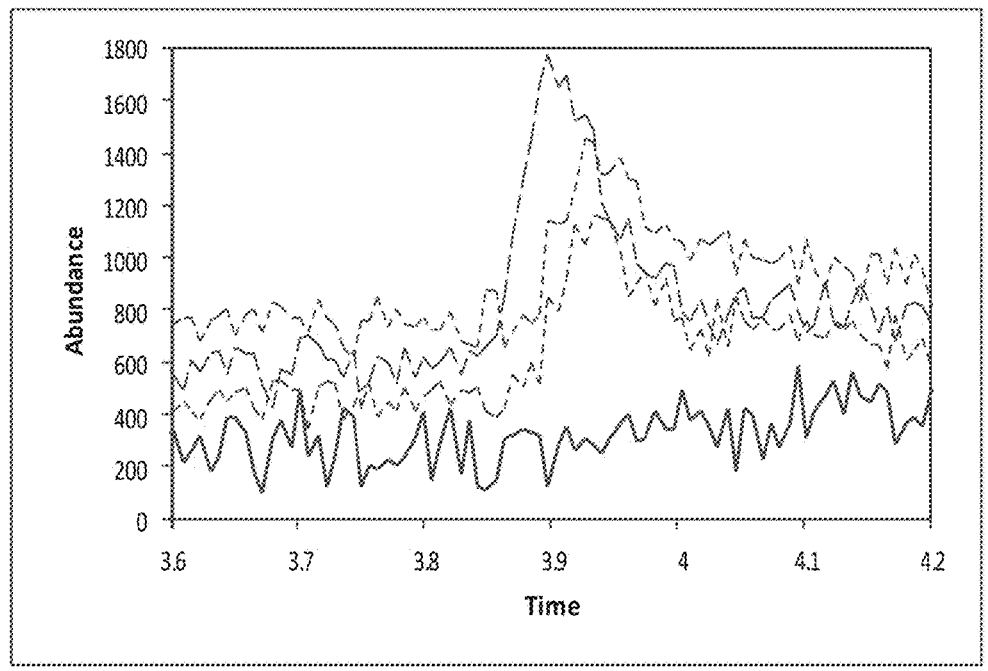
FIG. 13A indicates the level of detection for benzaldehyde using the present invention while FIG. 13B indicates the level of detection for benzaldehyde using SBSE.
Figure 13B:
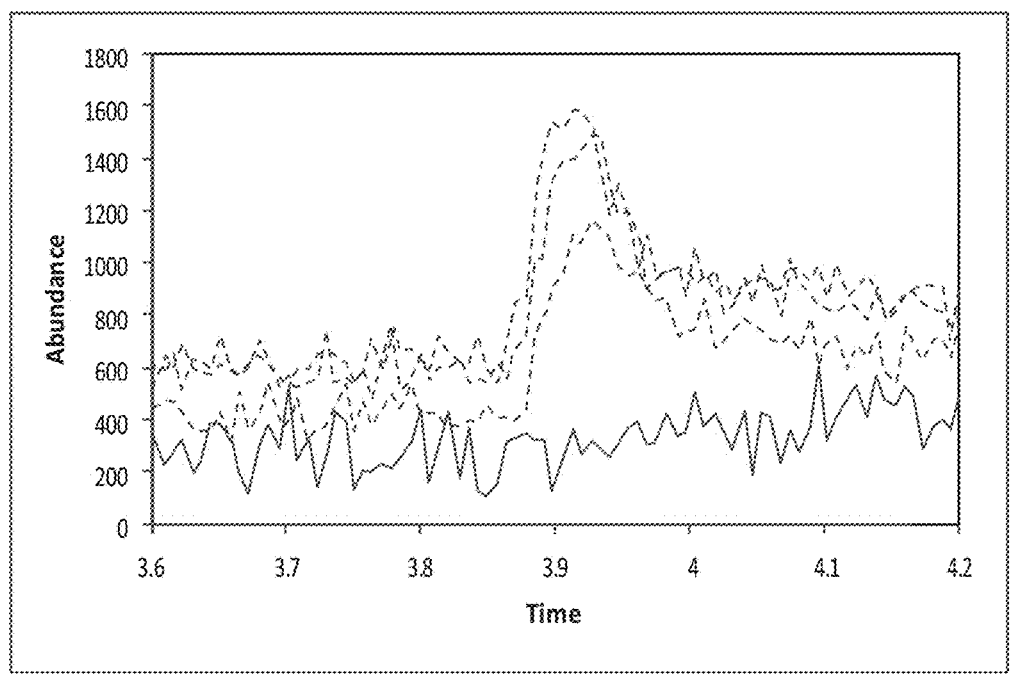
Figure 14:
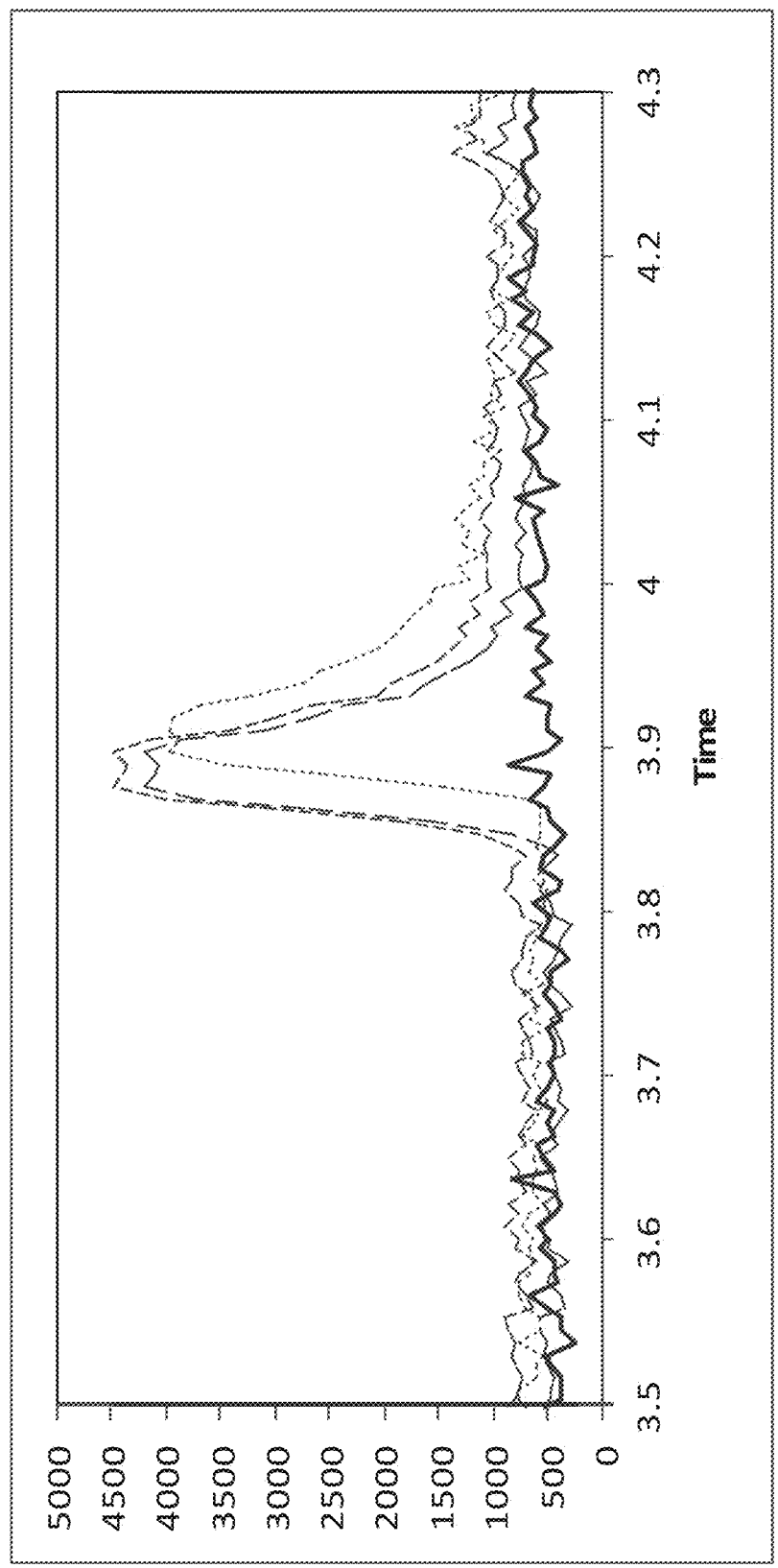
FIG. 14 illustrates the lower limit of qualification for SBSE.
Figure 15A:
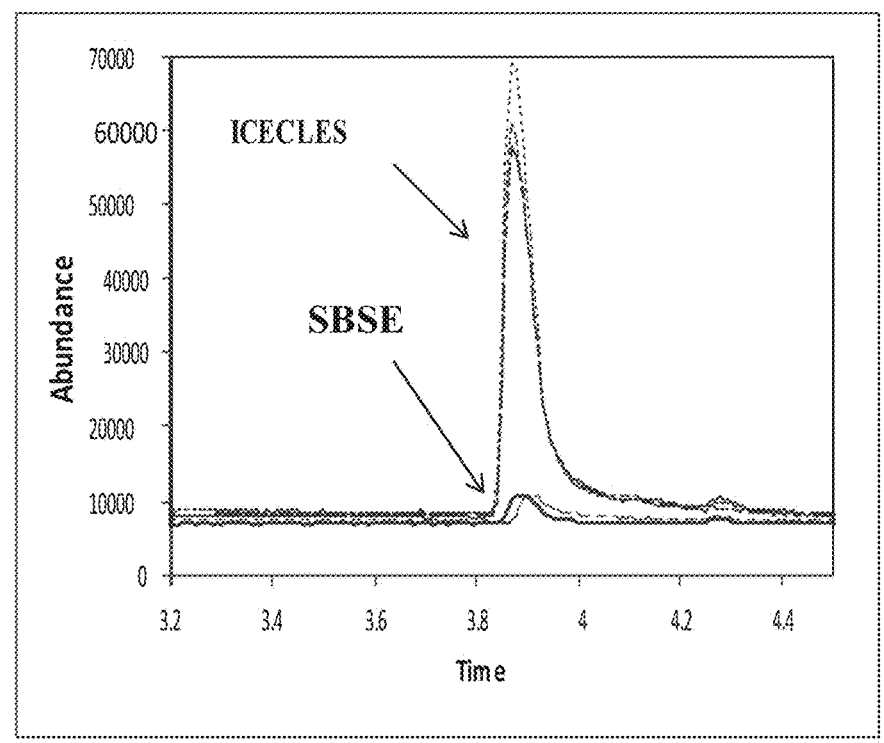
FIG. 15A indicates the concentration factor at the lower limit of qualification for the present invention and SBSE.
Figure 15B:
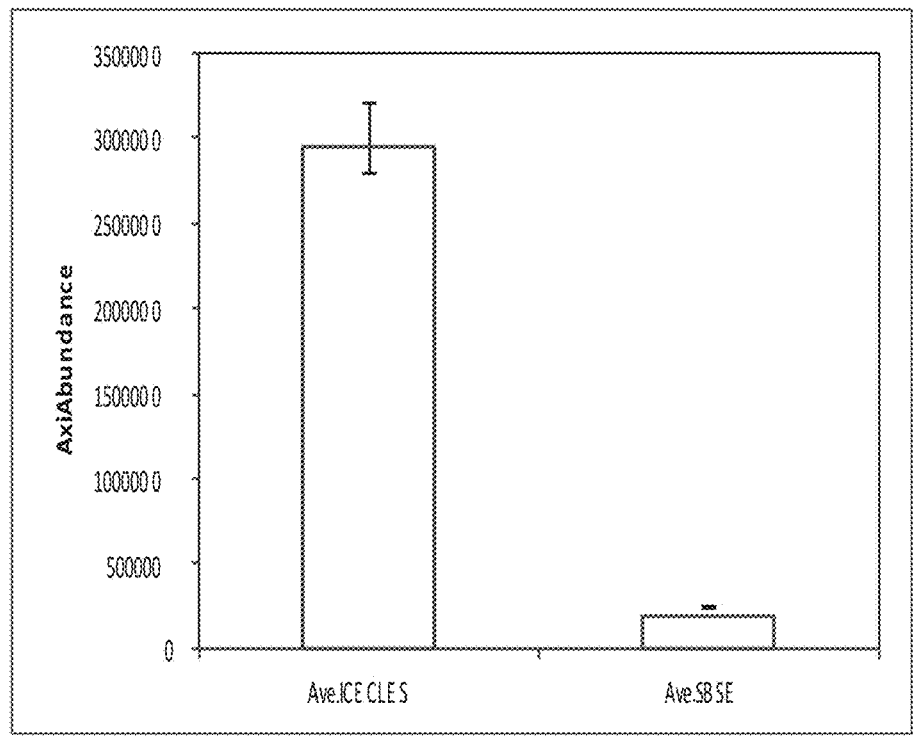
FIG. 15B shows that the lower limit of qualification of benzaldehyde for the present invention as compared to that of SBSE.

Two molecules: dimethyltrisulfide (DMTS; log $K_{ow}$=1.87) and benzaldehyde (BA; log $K_{ow}$, =1.48) were concentrated according to the methods and apparatus of the present invention. Aqueous samples (100 nM; 12.6 ppb for DMTS and 10.6 ppb for BA) were prepared by the methods of the present invention and also by SBSE. The results of both the present invention and SBSE were analyzed by GCMS. FIG. 7 indicates the results of the analysis based on peak area. The signals of both DMTS and BA were enhanced using the methods of the present invention. The present invention produced a concentration factor of three times and eight times for DMTS and BA, respectively, compared to SBSE. For example, FIG. 8 shows the comparative peaks for SBSE and the present invention. FIG. 9 indicates the concentration factors as a function of temperature for BA. FIG. 10 indicates that concentration factors decreased with the increase of stir speed. FIG. 11 illustrates the relationship between concentration and concentration factor. FIG. 12 indicates there is little to no correlation between the concentration factor and the solution concentration. The level of detection (LOD) for BA was also determined and is comparatively shown in FIGS. 13A and 13B. The LOD of BA was decreased five times using the methods of the present invention. Further FIG. 14 illustrates the lower limit of qualification for SBSE, while FIGS. 15A and 15B indicate the concentration factor at the lower limit of qualification for the present invention and SBSE. As shown, the lower limit of qualification for the present invention is much lower than that of SBSE. This is further shown in FIG. 15B. Thus, the methods of the invention are capable of detection of solutes and much lower concentrations than existing methods.

Example 3

Figure 16:
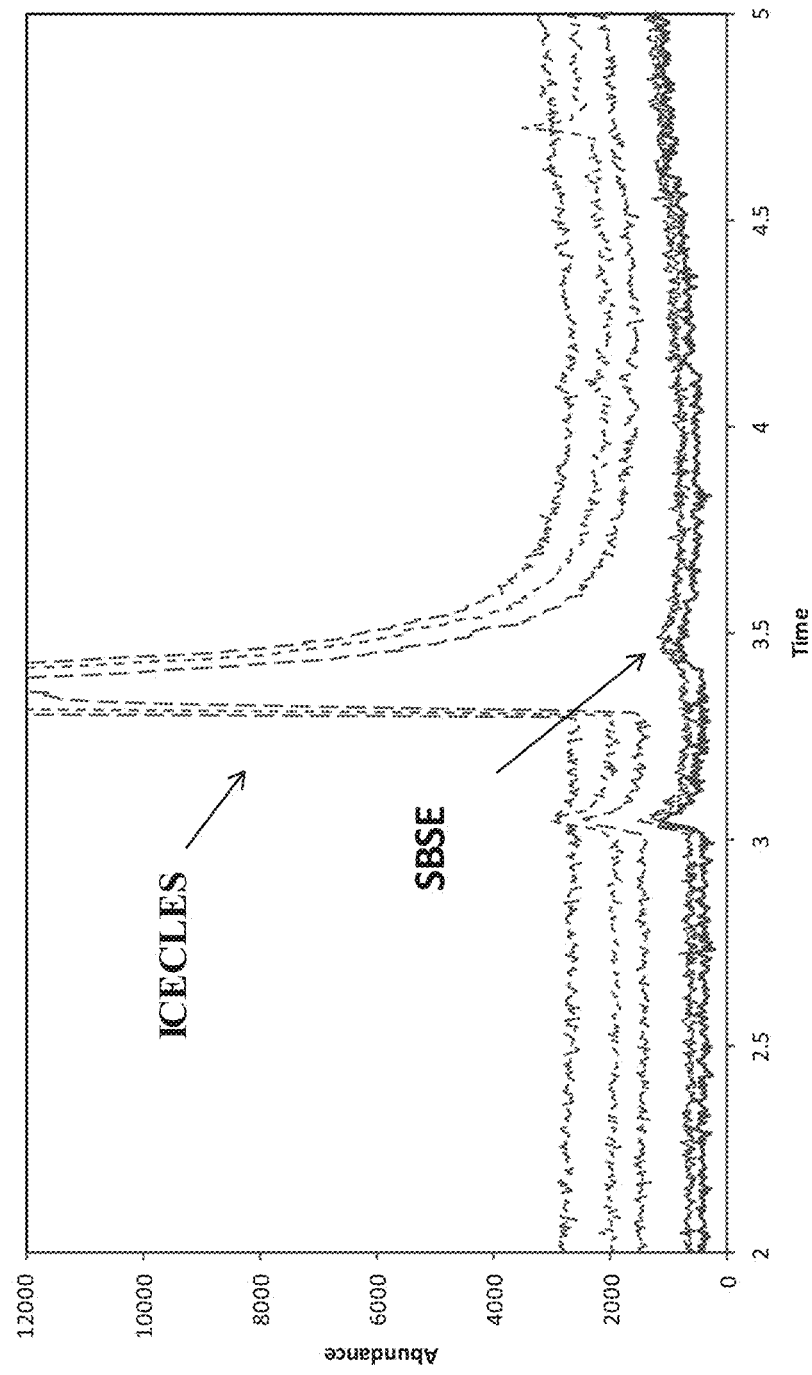
FIG. 16 illustrates the analysis of benzyl alcohol using the present invention as compared to SBSE.
Figure 17A:
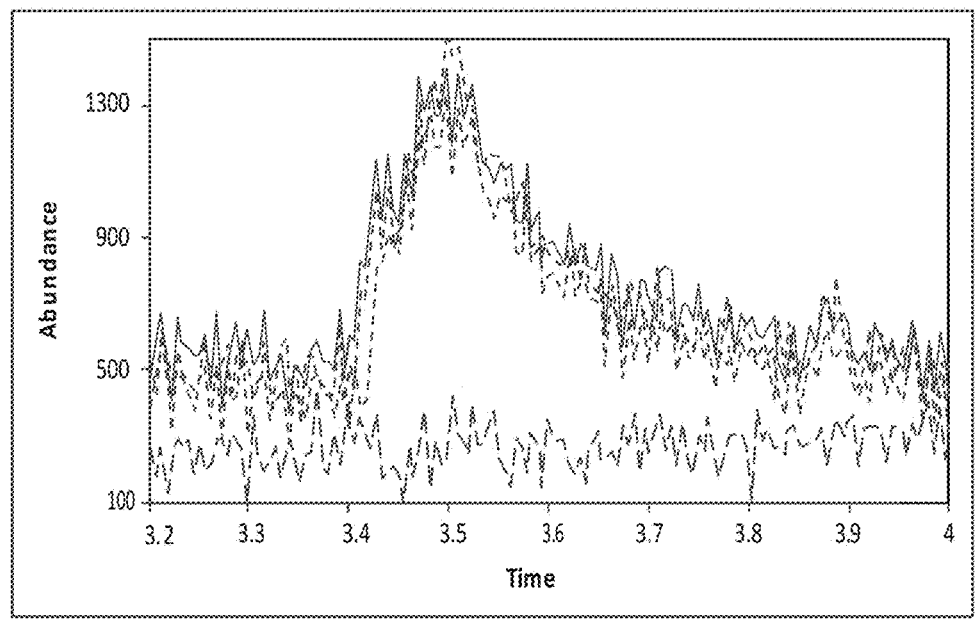
Figure 17B:
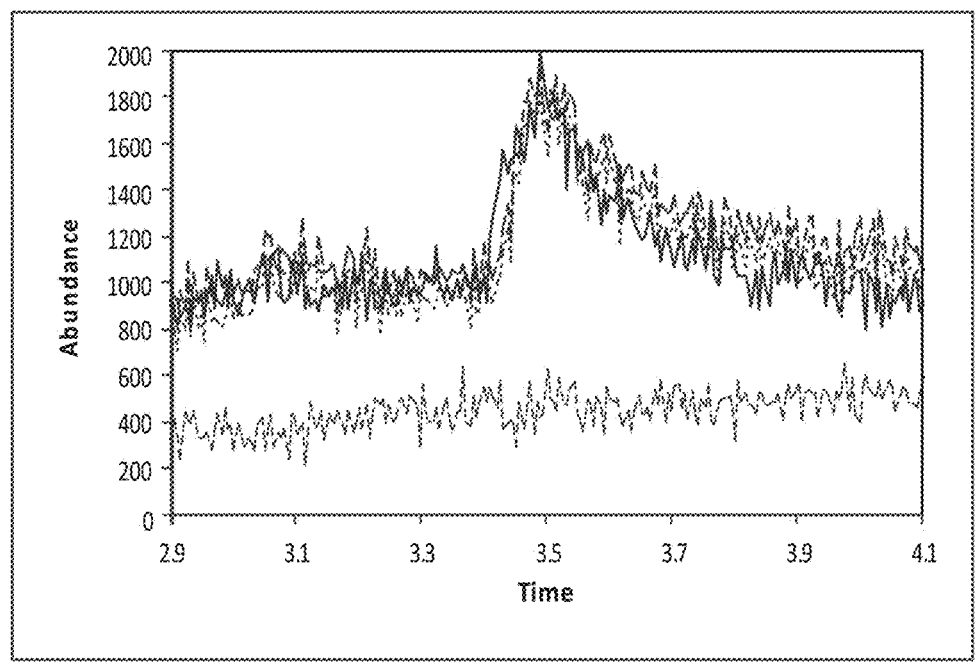
FIG. 17B shows the limit of detection of benzyl alcohol using SBSE.

Benzyl alcohol was analyzed according to the methods and apparatus of the present invention. Results of the present invention are compared to results of SBSE as shown FIG. 16. The limit of detection was also determined for both the present invention and SBSE for benzyl alcohol as shown in FIG. 17A and FIG. 17B, respectively. The LOD of benzyl alcohol extracted according to the methods of the present invention was approximately 40 nM as compared to 1 μM. Therefore, the LOD was decreased twenty-five times using the methods of the present invention. This Example further confirms that the methods of the invention are capable of detection of solutes and much lower concentrations than existing methods.

For the invention being thus described, it will be obvious that the same may be varied in many ways. Such variations are not to be regarded as a departure from the spirit and scope of the inventions and all such modifications are intended to be included within the scope of the following claims.

The above specification provides a description of the methods and apparatus of the present invention. Since many embodiments can be made without departing from the spirit and scope of the invention, the invention resides in the claims.

What is claimed is:

1. A method of extracting a solute from a liquid medium, comprising:
   stirring a liquid medium containing an analyte in a sample container with a sorptive stirrer comprising a sorptive material;
   cooling the sample container while the analyte is being stirred so the liquid medium freezes and the analyte is concentrated and absorbed into or adsorbed by the sorptive material, wherein said cooling is done by a cooling source; and
   simultaneously extracting the analyte into or by the sorptive material while the analyte is concentrated.

2. The method of claim 1, wherein said sorptive stirrer is an overhead stirrer or a magnetic sorptive stir bar rotated by a magnetic stir plate, magnetic U-shaped bracket, donut-shaped magnet, or electromagnetic field generator; and wherein said sorptive stirrer optionally comprises a chemically-inert coating, jacket, or layer.

3. The method of claim 2, wherein said magnetic U-shaped bracket or donut-shaped magnet rotates around said cooling source.

4. The method of claim 1, wherein said stirring step further comprises incrementally lowering the sample container into the cooling source.

5. The method of claim 1, further comprising a step of measuring variables of the method, wherein the measuring step measures temperature, speed of the sample container movement, speed of the sorptive stirrer, and combinations thereof.

6. The method of claim 1, further comprising a step of controlling the method using control software.

7. A method of extracting a solute from water, comprising:
stirring water containing an analyte in a sample container with a sorptive stirrer comprising a sorptive material;
cooling the sample container while the water is being stirred so the water freezes and the analyte is concentrated and absorbed into the sorptive stir bar; and
simultaneously extracting the analyte into or by the sorptive material while the analyte is concentrated.

8. The method of claim 7 further comprising identifying and/or quantifying the analyte with an analytical technique including one or more of the following: gas-chromatography and mass-spectroscopy (GCMS), thermal desorption GCMS, liquid chromatography, fluorometry, or spectroscopy.

9. The method of claim 8, further comprising quantifying the analyte in an amount of nanograms to femtograms.

10. The method of claim 9, wherein the cooling is performed by a cooling source, and wherein the sample container is placed in or on said cooling source.

11. The method of claim 10, wherein the cooling source is a cold bath, a jacketed beaker, a coolant, a cooled air system, a thermoelectric device, helium, or a nitrogen system.

12. The method of claim 11, wherein sorptive stirrer is a magnetic stir bar or overhead stirrer with a sorptive material; and wherein said sorptive stirrer optionally comprises a chemically-inert coating, jacket, or layer.

13. The method of claim 12, wherein the stirring is performed by a magnetic stir plate, a rotating magnetic U-shaped bracket, or a rotating magnetic donut-shaped component of an electromagnetic field generator that generates a rotating magnetic field around said sample container.

14. The method of claim 13, further comprising a step of lowering the sample container into the cooling source to facilitate freezing of the water.

15. The method of claim 14, wherein the lowering is performed by a stepper motor.

16. The method of claim 14, further comprising the step of measuring one and or more variables including temperature, speed of the sample container movement, speed of the stir bar, magnetic field strength and/or position, spectroscopic parameters, and/or combinations thereof.

17. The method of claim 16, further comprising controlling with a control software the temperature, speed of the sample container movement, speed of the stir bar, magnetic field strength and/or position, spectroscopic parameters, and/or combinations thereof.

* * * * *